(12) United States Patent
Nakama et al.

(10) Patent No.: US 12,048,787 B2
(45) Date of Patent: Jul. 30, 2024

(54) INFECTION PREVENTING DEVICE

(71) Applicant: NIKKISO CO., LTD., Tokyo (JP)

(72) Inventors: Takahiro Nakama, Tokyo (JP); Takahiro Akutsu, Tokyo (JP); Satoko Takigawa, Tokyo (JP)

(73) Assignee: Nikkiso Co., Ltd., Tokyo (JP)

( * ) Notice: Subject to any disclaimer, the term of this patent is extended or adjusted under 35 U.S.C. 154(b) by 634 days.

(21) Appl. No.: 17/417,229

(22) PCT Filed: Dec. 6, 2019

(86) PCT No.: PCT/JP2019/047937
§ 371 (c)(1),
(2) Date: Jun. 22, 2021

(87) PCT Pub. No.: WO2020/137465
PCT Pub. Date: Jul. 2, 2020

(65) Prior Publication Data
US 2022/0054699 A1    Feb. 24, 2022

(30) Foreign Application Priority Data
Dec. 25, 2018   (JP) .................. 2018-241094

(51) Int. Cl.
*A61L 9/20*       (2006.01)
*B64D 11/06*      (2006.01)
(Continued)

(52) U.S. Cl.
CPC .......... *A61L 9/205* (2013.01); *B64D 11/0626* (2014.12); *B64D 13/06* (2013.01);
(Continued)

(58) Field of Classification Search
CPC ............... A61L 9/205; A61L 2209/111; A61L 2209/12; A61L 2209/14; B64D 13/00;
(Continued)

(56) References Cited

U.S. PATENT DOCUMENTS

| 10,029,797 B2 | 7/2018 | Space et al. |
| 2014/0179212 A1 | 6/2014 | Space et al. |

FOREIGN PATENT DOCUMENTS

| FR | 3 028 453 A1 | 5/2020 |
| JP | 2-115642 A | 4/1990 |

(Continued)

OTHER PUBLICATIONS

International Search Report dated Feb. 4, 2020 issued in PCT/JP2019/043937.
(Continued)

*Primary Examiner* — Lessanework Seifu
(74) *Attorney, Agent, or Firm* — Scully, Scott, Murphy & Presser, PC

(57) ABSTRACT

An infection preventing device includes air barrier forming units that include an air inlet for taking in air from a rear in a front-rear direction, an air purification mechanism for creating clean air by purifying the air taken in from the air inlet, and an air outlet for blowing the clean air toward the front in the front-rear direction, and are capable of blowing out the clean air from the air outlet in the form of layer perpendicular to the left-right direction. The air barrier forming units provided on the seats adjacent in the front-rear direction face in the front-rear direction, and it is configured that air including clean air blown out of the air outlet of the rear air barrier forming unit can be taken in by the air inlet of the front air barrier forming unit.

6 Claims, 4 Drawing Sheets

(51) Int. Cl.
*B64D 13/06* (2006.01)
*F24F 7/003* (2021.01)

(52) U.S. Cl.
CPC ......... *F24F 7/003* (2021.01); *A61L 2209/111* (2013.01); *A61L 2209/12* (2013.01); *A61L 2209/14* (2013.01); *B64D 2013/0651* (2013.01)

(58) Field of Classification Search
CPC .... B64D 11/06; B64D 11/0626; B64D 13/06; B64D 2013/0651; B60N 2/879
See application file for complete search history.

(56) References Cited

FOREIGN PATENT DOCUMENTS

| | | |
|---|---|---|
| JP | 2004-225983 A | 8/2004 |
| JP | 2009-126349 A | 6/2009 |
| JP | 2001-30719 A | 2/2011 |
| WO | 2008/065709 A1 | 6/2008 |
| WO | 2018/163526 A1 | 9/2018 |

OTHER PUBLICATIONS

Translation of an International Preliminary Report on Patentability and Written Opinion dated Jul. 8, 2021 issued in PCT/JP2019/043937.
Extended European Search Report dated Aug. 25, 2022 from related EP 19 903 687.2.

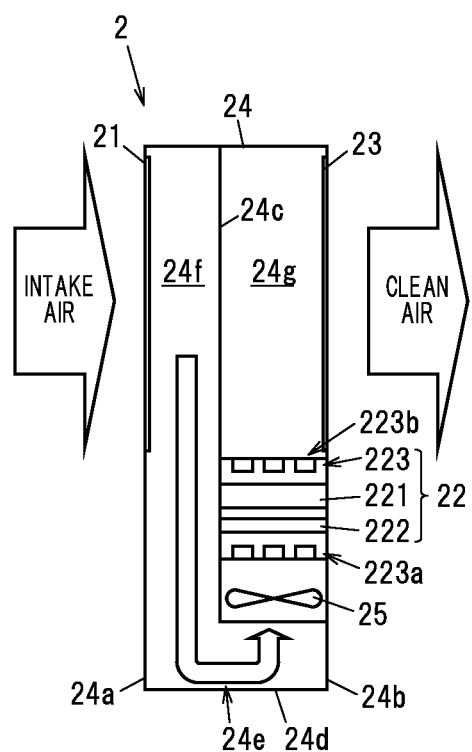
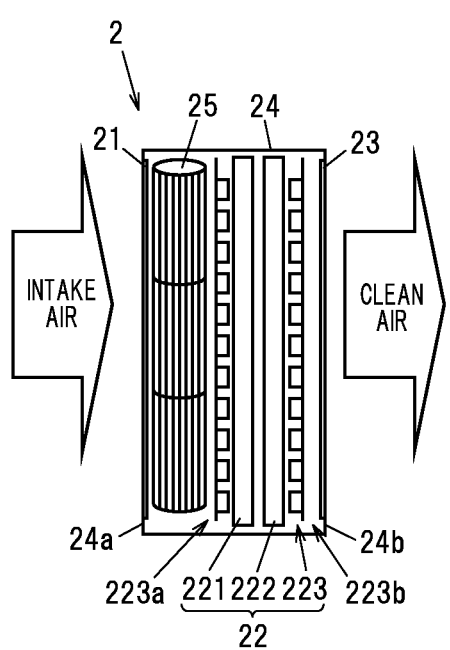

INFECTION PREVENTING DEVICE

TECHNICAL FIELD

The invention relates to an infection preventing device that is mounted on a vehicle for suppressing infection among passengers.

BACKGROUND ART

In vehicles such as aircraft, viral and bacterial infection among passengers is a problem. Patent Document 1 proposes a mechanism to supply clean air from a side part of a headrest of a seat to around the periphery of the face of a passenger sitting in the seat.

CITATION LIST

Patent Literature

Patent Document 1: U.S. Pat. No. 10,029,797, Specification

SUMMARY OF INVENTION

Technical Problem

The mechanism of Patent Document 1 has a structure in which clean air is supplied from a position close to ears of passengers. Therefore, when the supply amount of clean air is increased to suppress infection, passengers may feel uncomfortable since noise becomes loud and also the air hits the face. In addition, with the mechanism of Patent Document 1, it is difficult to prevent spread of bacteria or viruses released from a passenger in case that the position of the face moved such as when the passenger had a big sneeze or violent cough.

Therefore, it is an object of the invention to provide an infection preventing device capable of suppressing infection among passengers without making the passengers feel uncomfortable.

Solution to Problem

To solve the above-described problem, the invention provides an infection preventing device that is mounted, for suppressing infection among a plurality of passengers, on a vehicle comprising a plurality of seats for the plurality of passengers to sit, the plurality of seats being aligned in a front-rear direction and a left-right direction as viewed when seated in the seats, the infection preventing device comprising: air barrier forming units that comprise an air inlet for taking in air from the rear in the front-rear direction, an air purification mechanism for creating clean air by purifying the air taken in from the air inlet, and an air outlet for blowing the clean air toward the front in the front-rear direction, and are capable of blowing out the clean air from the air outlet in the form of layer perpendicular to the left-right direction, wherein the air barrier forming unit is provided at each of side ends of seat backs of the plurality of seats, the air barrier forming units provided on the seats adjacent in the front-rear direction face in the front-rear direction and it is configured that air including clean air blown out of the air outlet of the rear air barrier forming unit can be taken in by the air inlet of the front air barrier forming unit.

Advantageous Effects of Invention

According to the invention, it is possible to provide an infection preventing device capable of suppressing infection among passengers without making the passengers feel uncomfortable.

BRIEF DESCRIPTION OF DRAWINGS

FIG. 2A is a schematic configuration diagram illustrating a configuration example of the air barrier forming unit.

FIG. 2B is a schematic configuration diagram illustrating a configuration example of the air barrier forming unit.

DESCRIPTION OF EMBODIMENT

Embodiment

An embodiment of the invention will be described below in conjunction with the appended drawings.

Figure 1A:
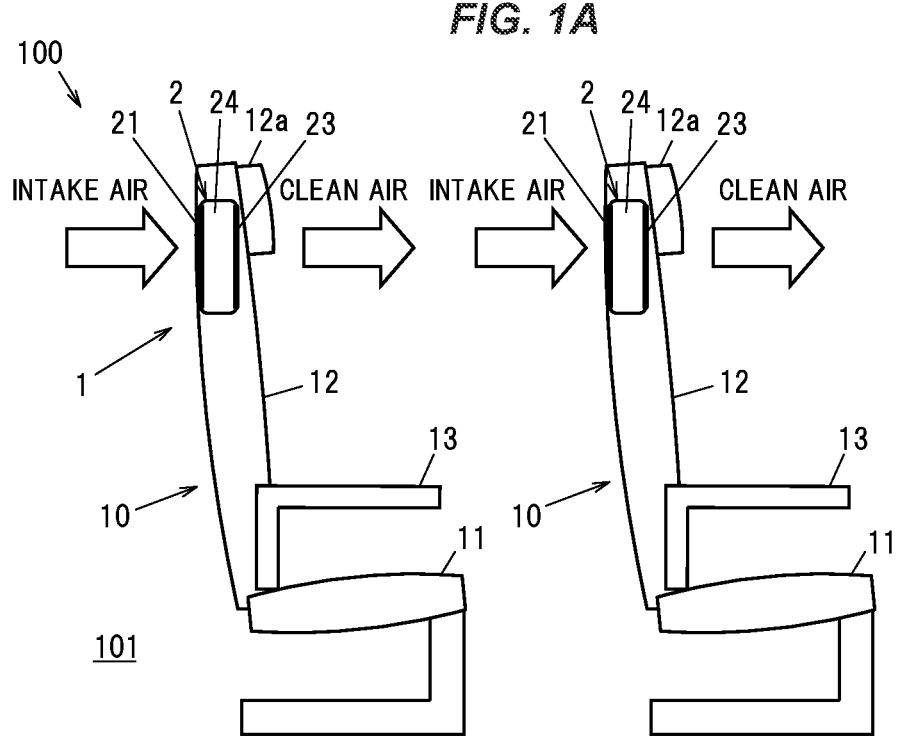
FIG. 1A is a diagram illustrating a cabin in an aircraft equipped with an infection preventing device in an embodiment of the present invention and is a side view of seats on which air barrier forming units are provided.
Figure 1B:
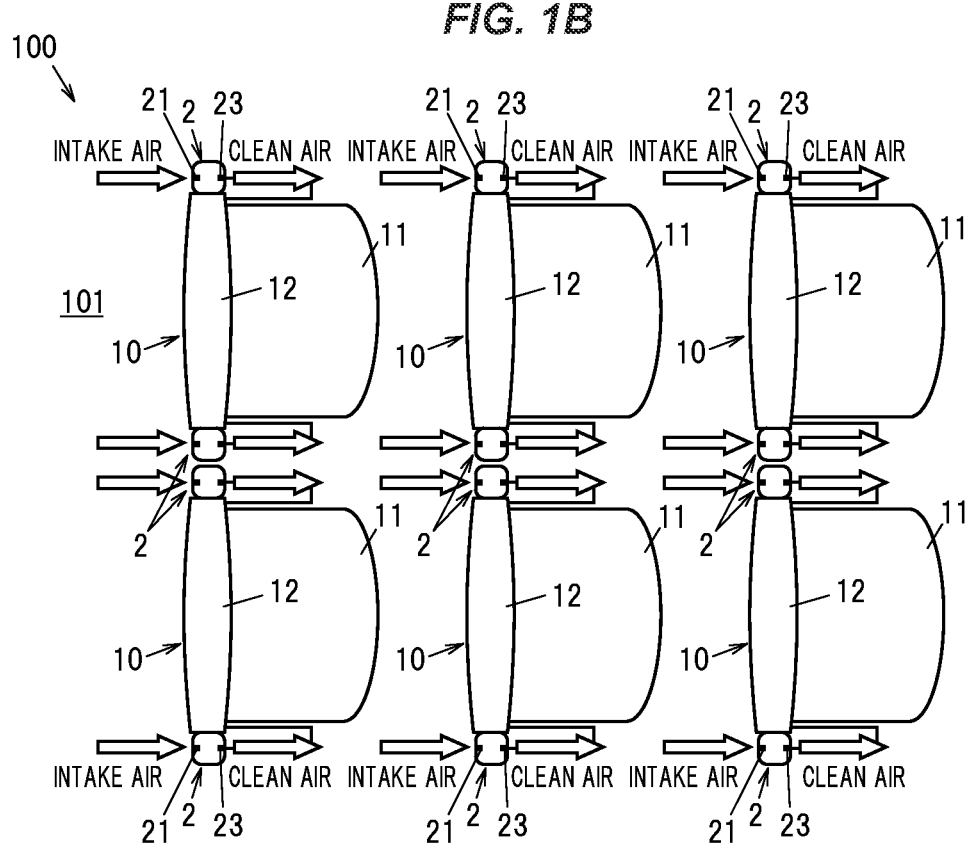
FIG. 1B is a top view of FIG. 1A.

FIG. 1A is a diagram illustrating a cabin in an aircraft equipped with an infection preventing device in the present embodiment and is a side view of seats on which air barrier forming units are provided. FIG. 1B is a top view of FIG. 1A. FIGS. 2A and 2B are schematic configuration diagrams illustrating configuration examples of the air barrier forming unit.

As shown in FIGS. 1A and 1B, an infection preventing device 1 is a device that is mounted on a vehicle 100 having plural seats 10 for plural passengers to sit and is to suppress infection among the plural passengers. Although an example in which the vehicle 100 is an aircraft will be described here, the vehicle 100 equipped with the infection preventing device 1 is not limited to the aircraft, and it is applicable to, e.g., a long-distance train such as bullet train or express train, or bus, etc. As will be described in detail later, the infection preventing device 1 can not only decompose and inactivate bacteria and viruses but also suppress odor and remove particulate matter (PM) and thus can be suitably used particularly in the vehicle 100 in which a large number of passengers are forced to spend a long time in a closed space.

The seat 10 has a seat surface 11 and a seat back 12 extending upward from a rear end of the seat surface 11. Armrests 13 are respectively provided on both sides of the seat surface. A headrest 12a is provided on an upper part of the seat back 12. The seat 10 may have a reclining function with which a tilt angle of the seat back with respect to the seat surface 11 can be adjusted.

Plural seats 10 are aligned in a cabin 101 of the aircraft. In more particular, the plural seats 10 are aligned in the front-rear direction and the left-right direction of the seat 10. Here, the seat back 12-side of the seat 10 is defined as rear and the opposite side is defined as front. In addition, a lateral direction of the seat 10, i.e., on the armrest 13-side, is defined as the left-right direction. Although the front-rear direction and the left-right direction of the vehicle 100 with respect to the travel direction coincide with the front-rear direction and the left-right direction of the seat 10 in general aircrafts (passenger airliner), it is not limited thereto, and the travel direction of the vehicle 100 and the front-rear direction or the left-right direction of the seat 10 may not coincide with each other. Hereinafter, each of front, rear, right, left and vertical directions represents a direction based on to the seat 10.

The infection preventing device 1 includes plural air barrier forming units 2 installed on each seat 10. As shown in FIGS. 1A, 1B and FIG. 2A, the air barrier forming unit 2 has an air inlet 21 for taking in air from the rear, an air purification mechanism 22 for creating clean air by purifying the air taken in from the air inlet 21, and an air outlet 23 for blowing the clean air toward the front.

The air inlet 21 is an opening provided on a back surface 24a of a case 24 housing the air purification mechanism 22, and is formed in a vertically extending slit shape. Likewise, the air outlet 23 is an opening provided on a front surface 24b of the case 24 and is formed in a vertically extending slit shape. From the air outlet 23, clean air is blown out in the form of layer perpendicular to the left-right direction (i.e., parallel to the vertical and front-rear directions).

A partition wall 24c is provided inside the case 24 to divide an inner space of the case 24 into front and rear sections. A lower end of the partition wall 24c is separated from a lower surface 24d of the case 24, so a gap 24e serving as an air flow path is formed between the partition wall 24c and the lower surface 24d. The air introduced into the case 24 from the air inlet 21 is guided downward through a space 24f on the rear side of the partition wall 24c, passes through the gap 24e below the partition wall 24c, is guided upward through a space 24g on the front side of the partition wall 24c, and is then discharged from the air outlet 23.

A fan 25 for sucking (taking in) and discharging (blowing out) air is provided in the space 24g on the front side of the partition wall 24c, and the air purification mechanism 22 is provided above the fan 25 (on the air outlet 23-side) in the space 24g.

The air purification mechanism 22 treats the air introduced from the air inlet 21 to decompose and inactivate bacteria and viruses and also suppress odor and remove particulate matter. The air purification mechanism 22 has a photocatalyst-supporting filter 222 collecting dust and supporting a photocatalyst exerting a photocatalytic effect when irradiated with ultraviolet rays, a collection filter 221 for collecting dust that passed through the photocatalyst-supporting filter 222, and a light source 223 for irradiating the photocatalyst-supporting filter 222 with ultraviolet rays.

In the present embodiment, a first light-emitting diode group 223a and a second light-emitting diode group 223b, which are formed by arranging ultraviolet light-emitting diodes in a planar shape, are used as the light source 223. Then, the photocatalyst-supporting filter 222 and the collection filter 221 are arranged between the two light-emitting diode groups 223a and 223b. The air purification mechanism 22 is formed by sequentially arranging the first light-emitting diode group 223a, the photocatalyst-supporting filter 222, the collection filter 221 and the second light-emitting diode group 223b from the air inlet 21-side (the lower side in the drawing) to the air outlet 23-side (the upper side in the drawing).

In the present embodiment, the two light-emitting diode groups 223a and 223b have different emission wavelengths. In particular, light-emitting diodes emitting deep ultraviolet light with a wavelength of not less than 250 nm and not more than 280 nm are used for the first light-emitting diode group 223a, and light-emitting diodes emitting ultraviolet light with a wavelength of not less than 360 nm and not more than 380 nm are used for the second light-emitting diode group 223b.

Furthermore, the photocatalyst-supporting filter 222 used in the present embodiment is configured such that an apatite-containing photocatalyst is supported on the first light-emitting diode group 223a-side and a titanium oxide-containing photocatalyst is supported on the second light-emitting diode group 223b-side. The ability to inactivate bacteria and viruses can be further enhanced by supporting the apatite-containing photocatalyst with a high ability to adsorb and inactivate bacteria and viruses on the first light-emitting diode group 223a-side where deep ultraviolet light with a wavelength of not less than 250 nm and not more than 280 nm, which has high sterilization ability but relatively low intensity, is emitted.

As the photocatalyst-supporting filter 222, it is possible to use a filter that has, e.g., a wall member dividing into a large number of spaces in a honeycomb shape and is configured that many photocatalytic particles are confined in each of the spaces divided by the wall member. The photocatalyst-supporting filter 222 is, e.g., a medium- to high-performance filter with a 0.4 μm particle collection efficiency of less than 99%.

As the collection filter 221, it is possible to use, e.g., a sub-HEPA filter (High Efficiency Particulate Air Filter) with a 0.3 μm particle collection efficiency of not less than 90%.

By using the air purification mechanism 22 having such a configuration, it is possible not only to decompose and inactivate bacteria and viruses but also to suppress odor by removing odor-causing substances and remove particulate matter, hence, it is possible to improve comfort of passengers. This air purification mechanism 22 can also decompose NOx, etc., and also can remove fine particles such as PM2.5.

Although it is not shown in the drawing, a light-blocking member for blocking ultraviolet light may be provided before and after the air purification mechanism 22. It is desirable to use a light-blocking member that blocks light but does not prevent the air from passing through, and it is possible to use, e.g., a member formed using plural perforated metals with a large number of holes that are overlapped at predetermined intervals so that the positions of the holes are staggered. In addition, although it is not shown in the drawing, a net-shaped or sponge-shaped coarse filter may be provided on the air inlet 21-side with respect to the photocatalyst-supporting filter 222.

In the air barrier forming unit 2 shown in FIG. 2A, since the air flow path inside the case 24 is narrow, the cost can be reduced by reducing the size of the fan 25 and the air purification mechanism 22 (the light-emitting diode groups 223a, 223b, the photocatalyst-supporting filter 222, the collection filter 221).

However, the specific configuration of the air barrier forming unit 2 is not limited thereto, and the air purification mechanism 22 may be configured such that, e.g., a vertical fan (line flow fan) is used as the fan 25, and the first light-emitting diode group 223a, the photocatalyst-supporting filter 222, the collection filter 221 and the second light-emitting diode group 223b are sequentially arranged from the air inlet 21-side (from the rear) to the air outlet 23-side (to the front), as shown in FIG. 2B. Since the direction of the flow path does not change in the case 24 in FIG. 2B, it is possible to reduce the size of the air barrier forming unit 2. Alternatively, plural vertically-arranged small fans can be used as the fan 25 instead of the vertical fan.

Referring back to FIGS. 1A and 1B, in the infection preventing device 1, the air barrier forming unit 2 is provided on each of both side ends of the seat backs 12 of the plural seats 10. Although the air barrier forming unit 2 provided so as to protrude to a side of the seat back 12 is shown here, the air barrier forming unit 2 may be built into the seat back 12. The air barrier forming unit 2 is provided slightly below the headrest 12a.

The infection preventing device 1 in the present embodiment is configured that the air barrier forming units 2 provided on the seats 10 adjacent in the front-rear direction face in the front-rear direction. Furthermore, it is configured that air including clean air blown out of the air outlet 23 of the rear air barrier forming unit 2 can be taken in by the air inlet 21 of the front air barrier forming unit 2.

Thus, even when the volume of the clean air blown out of the air outlet 23 is reduced, air barriers, i.e., barriers of air (also called air curtains) can be formed on both sides of the seat 10 by suction into the air inlet 21 of the front air barrier forming unit 2. The air barrier forming unit 2 can easily achieve quiet operation since the blowing amount of clean air is small, and in addition, wind does not directly hit the face, etc., of the passenger since the clean air is blown between the seats 10. Therefore, with the infection preventing device 1, it is possible to suppress entry of bacteria and viruses into a space bounded by the air barriers and suppress infection among passengers while maintaining quietness and thereby ensuring comfort of passengers.

In the present embodiment, the air barrier forming units 2 are respectively provided on both sides of each seat 10, as shown in FIG. 1B. In this case, two air barrier forming units 2 are arranged side by side between the adjacent right and left seats 10. In such a case, one of the air barrier forming units 2 may be omitted.

In addition, the air barrier forming unit 2 may also have an air volume adjustment mechanism capable of adjusting the blowing amount of clean air from the air outlet 23. The air volume adjustment mechanism is configured to be able to adjust the blowing amount of clean air by, e.g., adjusting a rotational speed of the fan 25 with a control of a driving current of the fan 25 or an appropriate control such as the PWM control.

The air volume adjustment mechanism may also be configured to be able to reduce the blowing amount of clean air from the air outlet 23 down to zero, i.e., able to stop blowing clean air (stop formation of an air barrier). For example, when configured such that an air exhaust port for blowing out air toward the upper or lower side of the case 24, which is normally closed, is provided and a control is performed in such a manner that the air exhaust port is opened and the air outlet 23 closed during when blowing of clean air is stopped, it is possible to stop blowing of clean air while continuously forming the air barrier for the rear seat 10 by continuously taking the air in from the air inlet 21. For example, when a couple or a parent and child are seated in the adjacent seats 10, the air barrier between their seats could be an obstacle. In such a case, the blowing amount of the air barrier forming units 2 between the seats is reduced down to zero so that the plural seats 10 as one unit form air barriers.

To adjust the air volume, a controller which can be operated by a passenger may be provided on the armrest 13, etc., of the seat 10 so that the air volume can be individually adjusted for each air barrier forming unit 2 (or each seat 10) by operating such a controller. It is also possible to disable individual adjustment of the air volume by passengers and to control the air volumes of all the air barrier forming units 2 in the cabin 101 all together.

Figure 3:
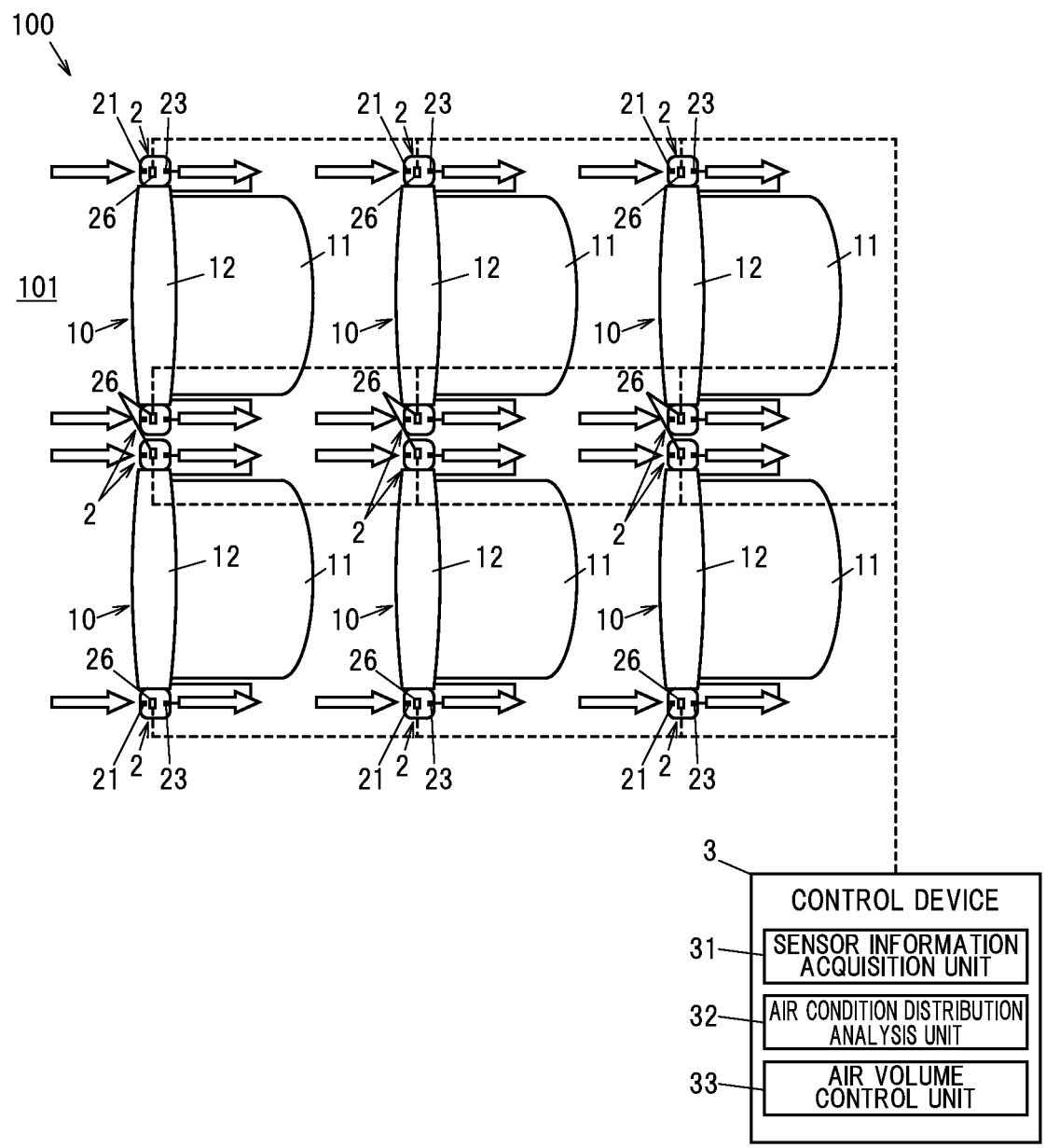
FIG. 3 is an explanatory diagram illustrating a sensor and a control device.

In addition, for example, a sensor 26 for detecting the condition of air taken in from the air inlet 21 may be provided on each air barrier forming unit 2, as shown in FIG. 3. As the sensor 26, it is possible to use any of a temperature sensor, a humidity sensor, an odor sensor and a dust sensor, or a combination of one or more thereof. In addition, a sensor capable of detecting viruses and bacteria will be able to be used as the sensor 26 in the future, even though it has not been put in practice yet.

In the example shown in FIG. 3, an output of each sensor 26 is sent to a control device 3. The control device 3 includes a sensor information acquisition unit 31 that acquires information from each sensor 26, and an air condition distribution analysis unit 32 that analyzes a distribution of the air condition (e.g., temperature distribution, odor distribution, etc.) in the cabin 101 based on the information acquired by the sensor information acquisition unit 31. The analysis result from the air condition distribution analysis unit 32 is recorded in a storage device, etc. (not shown). The analysis result stored in the storage device, etc., can be used for, e.g., development of a new airframe or design of aircraft air conditioning (air conditioning analysis), etc. In addition, by providing a display for displaying the analysis result in a cockpit, etc., it is possible to grasp the distribution of the air condition even in the cockpit, etc.

Furthermore, in the example in FIG. 3, the control device 3 is configured to automatically adjust the air volume (the blowing amount) of each air barrier forming unit 2. The control device 3 has an air volume control unit 33 that adjusts the air volume (the blowing amount) of each air barrier forming unit 2 based on the analysis result from the air condition distribution analysis unit 32. The air volume control unit 33 performs a control such that, e.g., the air volume (the blowing amount) of the air barrier forming units 2 is increased in an area where an odor detection value is high. As described above, by having the sensors 26 and the control device 3, it is possible to automatically control the air volume of each air barrier forming unit 2 while monitoring the status of the air. The sensor information acquisition unit 31, the air condition distribution analysis unit 32 and the air volume control unit 33 are realized by appropriately combining an arithmetic element such as CPU, a memory, a storage device, a software, and an interface, etc.

Figure 4A:
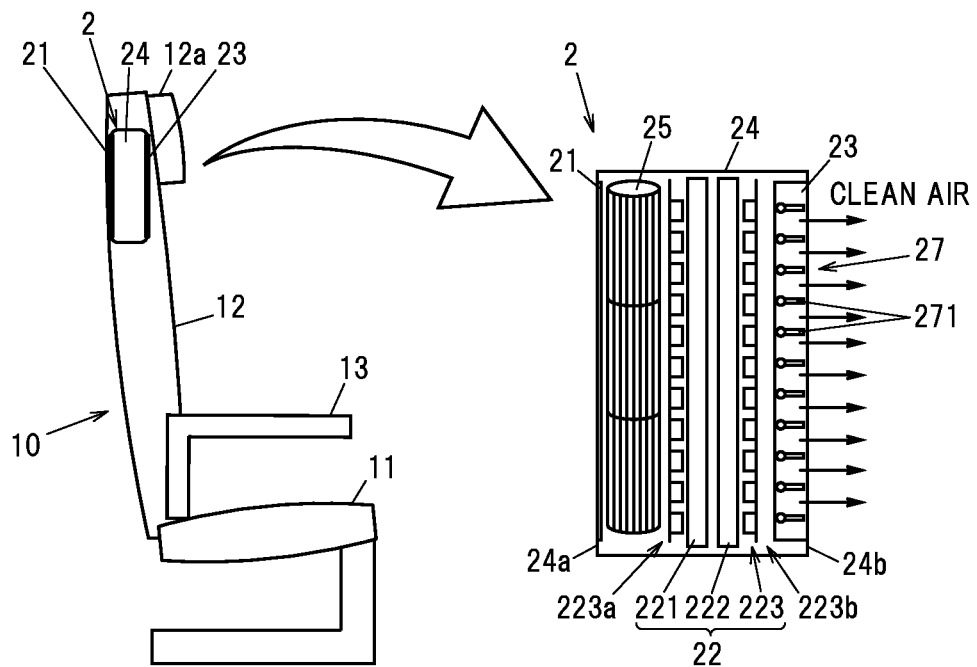
FIG. 4A is an explanatory diagram illustrating a blowing direction control mechanism.
Figure 4B:
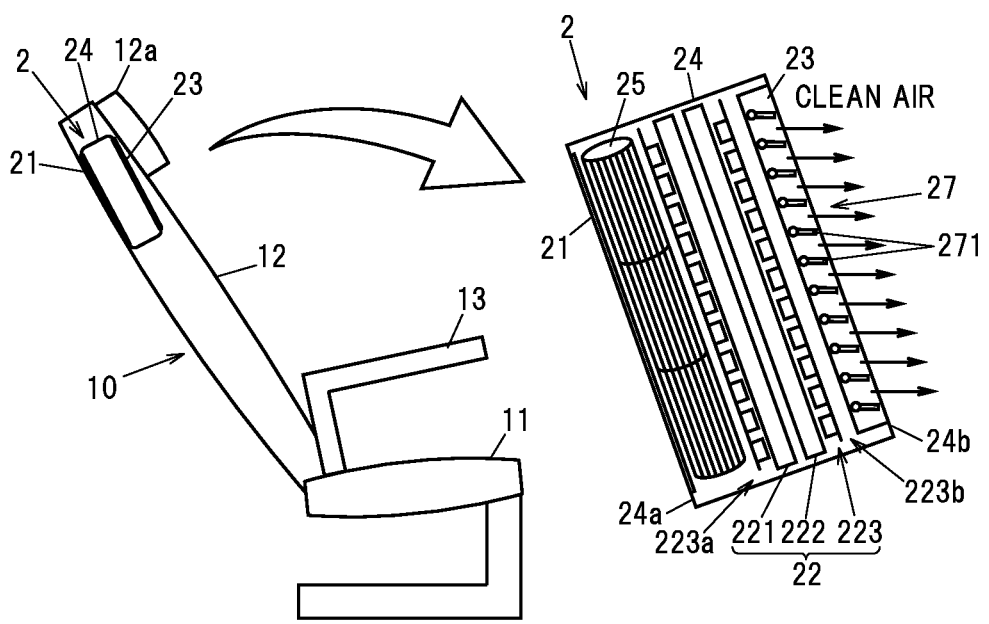
FIG. 4B is an explanatory diagram illustrating the blowing direction control mechanism.

The air barrier forming unit 2 may also have a blowing direction control mechanism 27 for controlling a direction of blowing clean air from the air outlet 23 according to a reclining angle of the seat back 12 (an angle formed between the seat surface 11 and the seat back 12), as shown in FIGS. 4A and 4B.

The blowing direction control mechanism 27 shown in FIGS. 4A and 4B has plural fins 271 that are provided at the air outlet 23 and are capable of controlling the blowing direction. By controlling the angle of the fins 271 according to the reclining angle of the seat back 12, it is possible to blow clean air forward regardless of the reclining angle. In case that a frame which does not move back even when reclining the seat back 12 is provided at a side end of the seat 10, the blowing direction control mechanism 27 can be omitted by providing the air barrier forming unit 2 on such a frame.

Functions and Effects of the Embodiment

As described above, the infection preventing device 1 in the present embodiment includes the air barrier forming units 2 each of which has the air inlet 21 for taking in air from the rear, the air purification mechanism 22 for creating clean air by purifying the air taken in from the air inlet 21, and the air outlet 23 for blowing the clean air toward the front, and which are capable of blowing out the clean air from the air outlet 23 in the form of layer perpendicular to the left-right direction, the air barrier forming unit 2 is provided at each of side ends of the seat backs 12 of the plural seats 10, the air barrier forming units 2 provided on the seats 10 adjacent in the front-rear direction face in the front-rear direction, and it is configured that air including clean air blown out of the air outlet 23 of the rear air barrier forming unit 2 can be taken in by the air inlet 21 of the front air barrier forming unit 2.

Even when the volume of air blown out of the air barrier forming unit 2 is reduced, the air barrier can be formed between the seats 10 by suction into the front air barrier forming unit 2. As a result, it is possible to suppress entry of bacteria and viruses into a space bounded by the air barriers and reduce a risk of infection among passengers while maintaining quietness and thereby ensuring comfort of passengers. The infection preventing device 1 can be applied only by installing the air barrier forming units 2 on the existing seats 10 or replacing seats of the vehicle 100 with the seats 10 provided with the air barrier forming units 2, and thus can be easily applied without changing the structure of the vehicle 100.

Summary of the Embodiment

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A infection preventing device (1) that is mounted, for suppressing infection among a plurality of passengers, on a vehicle (100) comprising a plurality of seats (10) for the plurality of passengers to sit, the plurality of seats (10) being aligned in a front-rear direction and a left-right direction as viewed when seated in the seats (10), the infection preventing device (1) comprising: air barrier forming units (2) that comprise an air inlet (21) for taking in air from the rear in the front-rear direction, an air purification mechanism (22) for creating clean air by purifying the air taken in from the air inlet (21), and an air outlet (23) for blowing the clean air toward the front in the front-rear direction, and are capable of blowing out the clean air from the air outlet (23) in the form of layer perpendicular to the left-right direction, wherein the air barrier forming unit (2) is provided at each of side ends of seat backs (12) of the plurality of seats (10), the air barrier forming units (2) provided on the seats (10) adjacent in the front-rear direction face in the front-rear direction, and it is configured that air including clean air blown out of the air outlet (23) of the rear air barrier forming unit (2) can be taken in by the air inlet (21) of the front air barrier forming unit (2).

[2] The infection preventing device (1) described in [1], wherein the air purification mechanism (22) comprises a photocatalyst-supporting filter (222) collecting dust and supporting a photocatalyst exerting a photocatalytic effect when irradiated with ultraviolet rays, and a light source (223) for irradiating the photocatalyst-supporting filter (222) with ultraviolet rays.

[3] The infection preventing device (1) described in [1] or [2], wherein the air barrier forming unit comprises a sensor (26) for detecting the condition of air taken in from the air inlet (21).

[4] The infection preventing device (1) described in any one of [1] to [3], wherein the air barrier forming unit (2) comprises an air volume adjustment mechanism capable of adjusting a blowing amount of the clean air from the air outlet (23).

[5] The infection preventing device (1) described in any one of [1] to [4], wherein the air barrier forming unit (2) comprises a blowing direction control mechanism (27) for controlling a direction of blowing the clean air from the air outlet (23) according to a reclining angle of the seat back (12).

[6] The infection preventing device (1) described in any one of [1] to [5], wherein the vehicle (100) comprises an aircraft.

Although the embodiment of the invention has been described, the invention according to claims is not to be limited the embodiment described above. In addition, all combinations of the features described in the embodiment are not necessary to solve the problem of the invention.

In addition, the invention can be appropriately modified and implemented without departing from the gist thereof. For example, although the air barrier forming unit 2 having one fan 25 has been described in the embodiment, it is not limited thereto. A fan for taking air in and a fan for blowing air out may be separately provided so that the amount of air suction (the intake air amount) and the amount of air blow (the blowing amount) can be controlled individually. In this case, it is possible to further improve quietness by setting the blowing amount of clean air to smaller than the intake air amount. Regarding a difference between the intake air amount and the blowing amount, it may be configured that, e.g., an air intake/exhaust port is provided at an upper part or a lower part of the case 24 so that the air can be taken in or discharged through the air intake/exhaust port.

In addition, although the air barrier forming unit 2 in the embodiment is configured to blow out clean air only in the vicinity of the headrest 12a, it is obviously possible to form a vertically long air barrier forming unit 2 extending to the lower part of the seat 10 (close to the seat surface 11) to widen the range in which an air barrier is formed.

Furthermore, although the example in which the air barrier forming units 2 are provided on each seat 10 has been described in the embodiment, the seats 10 not provided with the air barrier forming unit 2 may be included in the vehicle 100. For example, when three seats are provided side by side, the air barrier forming units 2 of the middle seat may be omitted and the air barrier forming units 2 may be provided only on the two seats 10 at the ends. In addition, instead of providing the air barrier forming units 2 at both side ends of each seat 10, a pair of the air barrier forming units 2 may be provided at both ends of a seat unit composed of plural seats 10 arranged side by side. That is, a pair of the air barrier forming units 2 may be provided every plural seats 10, and the layout of the air barrier forming units 2 can be appropriately changed.

REFERENCE SIGNS LIST

1: infection preventing device
2: air barrier forming unit
3: control device
10: seat
12: seat back 21: air inlet
22: air purification mechanism
222: photocatalyst-supporting filter
223: light source
23: air outlet
26: sensor
27: blowing direction control mechanism
100: vehicle

The invention claimed is:

1. An infection preventing device that is mounted, for suppressing infection among a plurality of passengers, on a vehicle comprising a plurality of seats for the plurality of passengers, the plurality of seats being aligned in a front-rear direction and a left-right direction as viewed when seated in the seats, the infection preventing device comprising:
air barrier forming units that comprise an air inlet for taking in air from the rear in the front-rear direction, an air purification mechanism for creating clean air by purifying the air taken in from the air inlet, and an air outlet for blowing the clean air toward the front in the front-rear direction, and are capable of blowing out the clean air from the air outlet in the form of layer perpendicular to the left-right direction,
wherein the air barrier forming unit is provided at each of side ends of seat backs of the plurality of seats, the air barrier forming units provided on the seats adjacent in the front-rear direction face in the front-rear direction, and it is configured that air including clean air blown out of the air outlet of the rear air barrier forming unit can be taken in by the air inlet of the front air barrier forming unit.

2. The infection preventing device according to claim 1, wherein the air purification mechanism comprises a photocatalyst-supporting filter collecting dust and supporting a photocatalyst exerting a photocatalytic effect when irradiated with ultraviolet rays, and a light source for irradiating the photocatalyst-supporting filter with ultraviolet rays.

3. The infection preventing device according to claim 1, wherein the air barrier forming unit comprises a sensor for detecting the condition of air taken in from the air inlet.

4. The infection preventing device according to claim 1, wherein the air barrier forming unit comprises an air volume adjustment mechanism capable of adjusting a blowing amount of the clean air from the air outlet.

5. The infection preventing device according to claim 1, wherein the air barrier forming unit comprises a blowing direction control mechanism for controlling a direction of blowing the clean air from the air outlet according to a reclining angle of the seat back.

6. The infection preventing device according to claim 1, wherein the vehicle comprises an aircraft.

* * * * *